(12) United States Patent
Ninomiya et al.

(10) Patent No.: US 6,303,359 B1
(45) Date of Patent: Oct. 16, 2001

(54) DNA MOLECULE ENCODING NEW AMINOPEPTIDASE, AND METHOD OF PRODUCING THE AMINOPEPTIDASE

(75) Inventors: Daiki Ninomiya; Tetsuya Miwa; Minao Asano; Nami Nakamura; Noriki Nio, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/525,046

(22) Filed: Mar. 14, 2000

(30) Foreign Application Priority Data

Mar. 15, 1999 (JP) .................................................. 11-068255

(51) Int. Cl.$^7$ ..................................................... C12N 9/48
(52) U.S. Cl. ......................... 435/212; 435/69.1; 435/219; 435/252.33; 435/320.1; 536/23.2; 536/23.6
(58) Field of Search .................................... 435/69.1, 212, 435/219, 252.33, 320.1; 536/23.2, 23.6

(56) References Cited

U.S. PATENT DOCUMENTS 5,824,534   10/1998   Asano et al. .......................... 435/212

FOREIGN PATENT DOCUMENTS

| 0 359 164 | 3/1990 | (EP) . |
| 0 939 131 | 9/1999 | (EP) . |
| 9-294583 | 9/1997 | (JP) . |
| WO 98/51804 | * 11/1998 | (WO) . |
| WO 99/57274 | 11/1999 | (WO) . |

OTHER PUBLICATIONS

T. Sasaki, Database Embl Nucleotide and Protein Sequences, D24588, Rice cDNA, parcial sequence (R2219_2A), 1 page, Nov. 29, 1993.

M. Asano, et al., Faseb Journal, vol. 11, No. 9, p. A1223, AN 2139, "Cysteine Proteases From Germinating Soybean Cotyledons, Which Contain 4–Hydoroxyproline", 1997.

J. M. Couton, et al., Plant Science (Limerick), vol. 75, No. 1, pp. 9–17, "Purification and Characterization of a Soybean Cotyledon Aminopeptidase", 1991.

R. Connor, et al., Database Embl Nucleotide and Protein Sequences, AC–036014, "Probabel Vacuolar Aminopeptidase I Precursor (EC 3. 4. 11. 22)", 1 page, Jun. 1, 1998.

R. Shoemaker, et al., Database Embl Nucleotide and Protein Sequences, 2 pages, AW234700, "GM–c1028–325 5' Similar to TR: Q9Z2W0 Aspartyl Aminopeptidase", Dec. 15, 1999.

R. Shoemaker, et al., Database Embl Nucleotide and Protein Sequences, AI748692, "GM–c1010–158 5' Similar to TR:036014 036014 Probable Vacuolar Aminopeptidase I Precursor; Mrna Sequence", 2 pages, Jun. 29, 1999.

R. Shoemaker, et al., Database Embl Nucleotide and Protein Sequences, 2 pages, AW279489, "GM–c1019–3393 5' Similar to TR:Q9Z2W0 Aspartyl Aminopeptidase; mRNA Sequence", Jan. 6, 2000.

R. Shoemaker, et al., Database Embl Nucleotide and Protein Sequences, 2 pages, AW704346, "GM–c1028–2514 5' Similar to TR: Q9Z2W0 Q9Z2W0 Aspartyl Aminopeptidase; mRNA Sequence", Apr. 19, 2000.

\* cited by examiner

Primary Examiner—Nashaat T. Nashed
Assistant Examiner—Christian L. Fronda
(74) Attorney, Agent, or Firm—Oblon, Spivak, McClelland, Maier & Neustadt, P.C.

(57) ABSTRACT

Disclosed are cDNA encoding a new aminopeptidase derived from germinated soybeans, a recombinant expression vector containing the DNA, a transformant obtained by the transformation with the expression vector, and a method of producing an aminopeptidase by culturing the transformed product.

According to the present invention, a cDNA can be obtained encoding the amino acid sequence of aminopeptidase GX suitable for producing a highly hydrolized product from a starting material containing a protein and peptide having a high acidic amino acid content. Using the cDNA, a recombinant aminopeptidase can be mass-produced with *E. coli* or the like. By using the cDNA, it is also possible to produce aminopeptidase GX by using a host other than *E. coli*. In addition, hydrohized products having high glutamic acid content and aspartic acid content and also excellent seasoning properties can be obtained from soybean protein by combining GX thus produced with protease D3 and leucine aminopeptidase DLAP.

17 Claims, 4 Drawing Sheets

DNA MOLECULE ENCODING NEW AMINOPEPTIDASE, AND METHOD OF PRODUCING THE AMINOPEPTIDASE

BACKGROUND OF THE INVENTION

The present invention relates to a DNA molecule encoding a new aminopeptidase derived from soybeans, a recombinant expression vector containing the DNA molecule, a transformant transformed with the recombinant expression vector, and a method of producing an aminopeptidase using the transformant.

Soybean protein is usually hydrolilzed into amino acids by the hydrolysis with an acid such as hydrochloric acid and sulfuric acid or with an existing proteases such as derived from a microorganism, e. g. an aspergillus.

However, when an acid proteolysis is used to obtain a proteolysis product of soybean protein which is useful as a natural seasoning, the reaction must be carried out at 100° C. for one or two days. The reaction at such a high temperature for such a long time causes a problem of a high energy consumption. Although the hydrolysis of protein with an acid is easy, it has other problems of excess decomposition (degradation) and high salts content caused by the neutralization.

To solve these problems, it was suggested to hdrolyze the soybean protein with the existing protease under mild reaction conditions. In particular, the hydrolysis of the soybean protein into amino acids with the proteoliytic enzymes (proteases) was expected to be a method which can be employed in place of the hydrolysis with acids by the chemical reaction, because the hydrolysis proceeds according to the biological reaction under mild reaction conditions.

However, storage protein in vegetables of the legume family is generally highly resistant to the existing proteases when the protein is native. Since existing proteases such as papain and subtihisin are typically endopeptidases, although they are capable of hydrolyzing protein into peptides, it is difficult to completely hcholyze the protein into amino acids using only these proteases. In addition, the product thus obtained cannot actually be used as the seasoning liquid because it tastes bitter.

It was considered that the combination of endopeptidases and exopeptidases such as aminopeptidase and carboxypeptidase, which are also the enzymes for hydrolyzing peptides into amino acids, is effective for solving the above-described problems.

On the other hand, it was reported that leucine aminopeptidase and acidic carboxypeptidase are important for increasing in amount of free amino acids in the hydrolysis of soybean protein with an aspergillus in, for example, the brewing of soy sauce [Tadanobu Nakadal, "Shoken" Vol. 11, No. 2 (1985)]. However, as suggested in this report, the soy sauce still contains (lipeptides and tiipeptides containing acidic amino acids in the sequences thereof, and the difficulty of the hydrolysis of them was pointed out. The dipeptides and tripeptides also include peptides having glutamic acid or aspartic acid at the N-terminal thereof. The difficulty in the hydrolysis of the peptides indicates that the substrate specificity of the peptidase is low for these peptides. In addition to the problem of the difficult hydrolysis of peptides with the peptidase derived from the aspergillus in the brewing of soy sauce, commercially available peptidase preparations also have a problem that the hydrolysis activity of microbial enzymes, such as the enzyme from Aspergillus, is also low for dipeptides and tripeptides containing acidic amino acids.

Under these circumstances, the inventors tried to solve the above-described problems by using soybean cotyledons. Namely, the storage protein in soybean seeds is hdrolyzed into amino acids in a very short period of time in the course of the germination of the seeds. From this phenomenon, it is supposed that peptidases capable of easily hydiohzing the poorly hyohizable peptides of the storage protein exist in the germinating soybeans. The inventors had found such peptidases (aminopeptidase GX and leucine aminopeptidases, which are capable of efficiently hydrolizing acidic amino acid-containing peptides) in germinated soybean cotyledons, and succeeded in efficiently hydrolyzing the soybean protein [Japanese Patent Unexamined Published Application (hereinafter referred to as "JP-Kokal") No.9-294583].

However, it was difficult to obtain a large amount of soybean aminopeptidase GX from an extract from germinated soybean cotyledons because soybean aminopeptidase GX content of these cotyledons is only very low.

In one of the methods of solving the above-described problems, aminopeptidase genes are strongly expressed by a genetic recombination technique by using a system other than soybeans to obtain a large amount of the aminopeptidase. To carry out this method, it is essential to obtain the cDNA encoding the aminopeptidase and to analyze the DNA sequence thereof, to obtain an information of the whole amino acid sequence of the aminopeptidase.

It is also indispensable that DNA encoding the aminopeptidase is integrated into a suitable expression vector to obtain a transformant capable of producing the intended product in a large amount.

SUMMARY OF THE INVENTION

The present invention has been completed under these circumstances. The object of the present invention is to provide a technique for the efficient gene expression and mass-production of the aminopeptidase using gene recombination techniques, which is to be employed in place of the above-described natural method of isolating aminopeptidase from germinated soybean cotyledons from natural origin.

After intensive investigations made for the purpose of solving the above-described problems, the inventors succeeded in obtaining cDNA encoding aminopeptidase GX by screening cDNA library prepared from germinated soybean shoot MRNA by using like plant EST the probe which has an internal amino acid sequence highly homologous to that of aminopeptidase GX.

After further investigations, the inventors have succeeded in obtaining a transformant capable of forming the aminopeptidase from cDNA thus obtained, and then obtaining a protein having the aminopeptidase activity.

Namely, the present invention provides the following:

(1) A DNA molecule encoding a new aminopeptidase derived from germinated soybean cotyledons having an amino acid sequence of SEQ ID No:2 in the sequence list.

(2) A recombinant DNA molecule containing the DNA molecule.

(3) A transformant transformed with the recombinant DNA molecule.

(4) A method of producing a protein having an aminopeptidase activity, which comprises culturing the transformant to produce a protein having the aminopeptidase activity, and recovering the same.

After intensive investigations made for the purpose of solving the above-described problems, the inventors succeeded in obtaining cDNA encoding aminopeptidase GX by screening cDNA library prepared from germinated soybean shoot mRNA by using rice plant EST as the probe which has an internal amino acid sequence highly homologous to that of aminopeptidase GX.

DESCRIPTION OF THE PREFERRED EMBODIMENTS OF THE INVENTION

Figure 1:
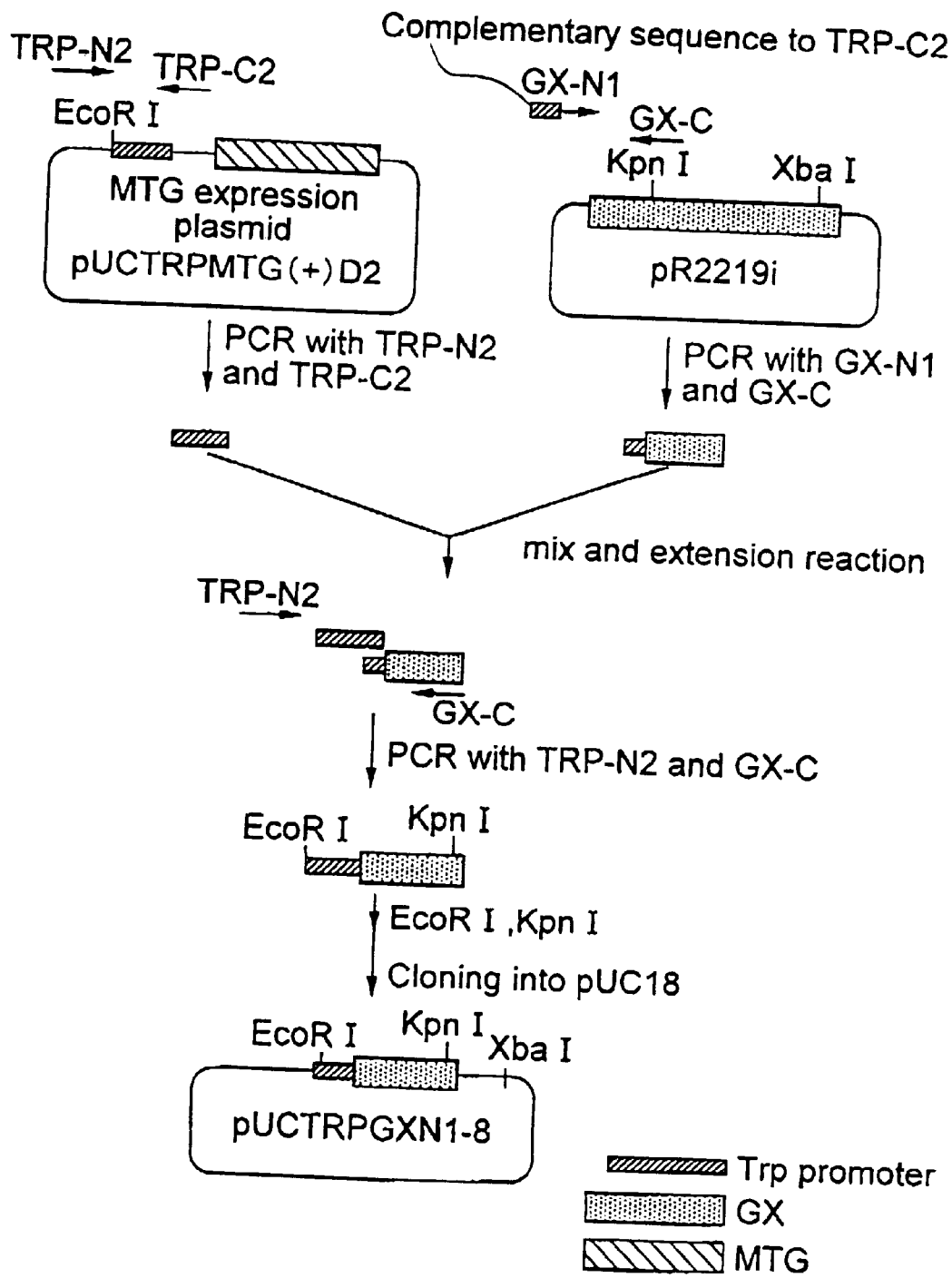
FIG. 1 shows the strategy for construction of plasmid pUCTRPGXN 1-8.

The present invention provides the followings:
(1) A DNA molecule encoding a new aminopeptidase derived from germinated soybean cotyledons having an amino acid sequence of SEQ ID NO:2 in the sequence list.
(2) Variants of DNA molecule of (1) encoding the variants of the proteins having an amino acid sequence of SEQ ID NO:2 in which one or more amino acid residues are inserted, added, deleted or replaced.
(3) The DNA molecule of (1), which has a DNA sequence ranging from base No.22 to base No. 1428 in SEQ ID NO:1 in the sequence list.
(4) A recombinant D)NA molecule containing the DNA molecule of any of (1) to (3).
(5) A transformant transformed with the recombinant DNA molecule.
(6) A method of producing a protein having an aminopeptidase activity, which comprises culturing the transformant to produce a protein having the aminopeptidase activity, and recovering the same.

The detailed description will be made on the present invention. Aminopeptidase GX will be referred to as "GX" hereinafter.

<1> DNA Molecule of the Present Invention:

cDNA of the present invention can be obtained by, for example, an ordinary method wherein an oligo-DNA is synthesized on the basis of an already determined amino acid sequence of GX, gene segments are prepared by using mRNA extracted from germinated soybean cotyledons or another portion thereof as a template for RT-PCR method, and cDNA for GX is cloned by the hybridization using the gene segments as probes, from cDNA library prepared from mRNA of the cotyledons or another portion of the germinated soybeans as the template.

In another possible method, a DNA sequence highly homologous to that encoding the already determined amino acid sequence of GX is retrieved from a suitable DNA data base such as DDBJ, EMBL or GenBank, a cDNA library was prepared using MRNA extracted from the cotyledons or another portion of the germinated soybeans as a template, and the cDNA library is screened to obtain cDNA of GX using the DNA segment of corresponding sequence as the probe.

The kind of the soybeans to be germinated for the extraction of mRNA from GX is not limited. Namely, the cultivating area and variety of soybeans are not limited; and commercially available soybeans, those used as a material for squeezing soybean oil, etc. are usable. Further, the method of the germination, culture conditions, stage (germinated or non-germinated) and duration of the germination of them are not limited. It is preferred, however, to use germinated soybeans obtained by growing them for 7 to 10 days, after soaking soybean seeds in water.

The probe for cDNA can also be prepared by RT-PCR method or the like on the basis of an already determined amino acid sequence by using mRNA extracted from the cotyledons or another portion of germinated soybean cotyledons; or by chemically synthesis on the basis of the amino acid sequence. A DNA sequence highly homologous to the amino acid sequence is usable as the probe, regardless of the origin of the DNA sequence and the function of the gene product. Namely, the DNA sequence is not limited to that of a known aminopeptidase; the gene product having an unknown function is also usable; and EST (Expression Sequence Tag) is also usable. In the Examples given below, EST derived from rice plant roots was used as the probe. The cDNA library can be produced by an ordinary method.

Thus, DNA molecule encoding the new aminopeptidase derived from germinated soybean cotyledons and having an amino acid sequence of SEQ ID NO:2 in the sequence list can be obtained. DNA molecule of the present invention may be the one which encodes a protein having an amino acid sequence of SEQ ID No:1 in the sequence list, in which one or more amino acid residues are inserted, added, deleted or replaced, so far as the protein encoded by the DNA molecule has the aminopeptidase activity.

After further investigations, the inventors have succeeded in obtaining a transformant capable of forming the aminopeptidase from cDNA thus obtained, and then obtaining a protein having the aminopeptidase activity.

<2> Recombinant DNA Molecule of the Present Invention:

cDNA thus obtained is integrated into an expression vector to obtain a recombinant DNA molecule. The vector to be used is not particularly limited. The vector may be the one capable of autonomously replicating in the host cells or the one capable of being inserted in the chromosome in more than one copy. The vector must have an insertion site in which the above-described DNA, i.e. GX gene, can be inserted and further a region which allows the inserted DNA to be expressed in the host cells.

The GX genes to be inserted into the vector are not limited to only cDNA but they also include DNA fragments designed so as to code the amino acid sequence of GX deduced from cDNA. The genes deduced from such an amino acid sequence can be easily synthesized by ligating an oligonucleotide synthesized with an automatic DNA synthesizing machine after the annealing.

In another method, GX is expressed and produced in the form of a fused protein associated with an heterologous protein. For example, GX can be produced in *Escherichia coli* (*E. coli*) in the form of a fused protein, linked to glutathione-S-transferase using pGEX system (a product of Amersham Pharmacia Biotech. Co.) or the like.

As promoters for expressing the GX genes, strong promoters usually used for the expression of heterologous proteins can be used. A terminator can be introduced into a downstream of the GX gene. The examples of promoters include, for example, trp, tac, lac, trc, λPL and T7, and the terminators include, for example, tpA, lpp and T4.

For making the translation more efficient, the variety and number of SD sequence, and the base composition, sequence and length in the region between the SD sequence and the initiation codon are preferably optimized for the expression of GX gene.

The region between the promoter and the translation-initiating point, required for the expression of GX, can be prepared by a well-known PCR method or chemical synthesis method. An example of the sequences is shown in SEQ ID NO:3.

The recombinant DNA molecule of the present invention can be obtained by inserting the above-described GX gene-containing DNA fragment into a well-known expression vector selected depending on the intended expression system. The expression vector used herein is preferably a multi copy vector.

Known vectors usable for the preparation of the recombinant DNA molecule of the present invention are pUC18, pHSG299, etc. An example of the recombinant DNA molecule of the present invention is pUCTRPGX1-8, which is obtained by integrating DNA molecule of the present invention into pUC 18.

<3> Transformant of the Present Invention:

The description will be made on various transformants obtained by the introduction of the above-described recombinant DNA molecule.

The cells which can be converted into the transformants are those of bacteria, such as *E. coli* or the like. Examples of *E. coli* strain include JM 109 strain (recA, endA1, gyrA96, thi, hsdR17, supE44,r elA1, and Δ(lac-proAB)/F' [traD36, proAB+, lacIq and LacZΔM15]).

The other cells which can be converted into the transformants are those of Bacillus subtills, yeast, Aspergillus, etc. It is possible to produce GX into a medium, taking advantage of the protein-secreting properties of them. In addition to the above-described microorganisms, cultured cells such as those of silk worms are also usable.

Then the recombinant vector obtained as described above is introduced into a host cell to obtain the transformant. The recombinant vector can be introduced into the host cell by various conventional methods, for example, competent cell method, protoplast method, calcium phosphate coprecipitation method, electroporation method, microinjection method and liposome fusion method.

<4> Method for Producing the Aminopeptidase of the Invention:

The transformant thus obtained is cultured to produce GX in the culture mixture. GX is isolated by a well-known method and, if necessary, purified to obtain the intended enzyme.

When *E. coli* is used as a host, it is possible that GX gene product is obtained as an inert GX association product, i. e. protein inclusion body, and then this inclusion body is activated by a suitable method. After the re-activation, the active protein can be separated and purified by a well-known method to obtain the intended enzyme.

The media for culturing the transformant are well known. For example, for culturing *E. coli*, a nutrient medium such as LB medium or a minimal medium such as M9 medium is used with the addition of a carbon source, a nitrogen source, a vitamin source, etc. The transformant is cultured at a temperature of usually 16 to 42° C., preferably 25 to 37° C., for 5 to 168 hours, preferably 8 to 72 hours. The culture conditions vary depending on the host. Both shaking culture and standing culture are possible. If necessary, the medium may be stirred or aerated. When a inducible promoter is used for expressing GX, a promoter inducer can be added to the medium.

GX can be isolated and purified from the extract of transformant by a well-known method such as salting-out method, isoelectric precipitation method or solvent precipitation method; a method wherein a difference in the molecular weight is utilized such as dialysis, ultrafiltration or gel filtration; a method wherein a specific affinity is utilized such as ion exchange chromatography; a method wherein a difference in the hydrophobicity is utilized such as hydrophobic chromatography or reversed phase chromatography; affinity chromatography; SDS polyacrylamide electrophoresis; or isoelectric focusing method. GX can be purified by a combination of these methods.

According to the present invention, a cDNA can be obtained encoding the amino acid sequence of aminopeptidase GX suitable for producing a highly hydrolyzed product from a starting material containing a protein and peptide having a high acidic amino acid content. Using the cDNA, a recombinant aminopeptidase can be mass-produced with *E. coli* or the like. By using the cDNA, it is also possible to produce aminopeptidase GX by using a host other than *E. coli*. In addition, hychohzed products having high glutamic acid content and aspartic acid content and also excellent seasoning properties can be obtained from soybean protein by combining GX thus produced with commercially available proteases such as Flavourzyme™ (manufactured by Novo Nordisk A/S) and Protease M™ (manufactured by Amano Pharmaceutical Co., Ltd.).

protease D3 and leucine aminopeptidase DLAP.

EXAMPLES

The following Examples is provided to only illustrate the present invention and not to limit the scope of the present invention to these examples.

Example 1

Cloning of GX cDNA:

In this Example, the present invention will be described on <1> determination of internal amino acid sequence of GX, <2> search for a DNA sequence having a high homology to that of GX, <3> analysis of GX expression site in soybeans and <4> screening of cDNA library of germinated soybean shoots using rice plant EST R2219_2A as the probe.

<1> Determination of Internal Amino Acid Sequence of GX:

GX protein obtained from germinated soybean cotyledons was reduced, carboxymethylated and treated with lysyl endopeptidase (EC. 3. 4. 21. 50 Wako Pure Chemical Industries, Ltd.). Peptide fragments thus obtained were taken with μRPC C2/C18 SC2.1/10 column (a product of Pharmacia Aktiebolag). The amino acid sequences of 10 portions of the fragment in total was successfully determined using a protein sequencer, after analyzing the amino acid sequence of each fragments.

<2> Search for DNA Sequence having High Homology to GX:

The amino acid sequences determined as described above were subjected to the homology retrieval of DDBJ (DNA DATA BANK of JAPAN) to find EST R2219_2A derived from rice plant roots and having a high homology to peptide fragment No. 8 of SEQ ID NO:4 in the sequence list. It is highly possible that R2219_2A of rice plant thus obtained is encoding GX homologue of rice plant. Then, the cloning of soybean GX was tried by using R2219_2A of rice plant as the probe. Before the cloning, the investigations were made to find a organ of the soybeans in which the expression was remarkable.

<3> Analysis of GX Expression Site in Soybeans:

Fragments of lice plant R2219_2Ac DNA to be used as the probes were obtained by RT-PCR method as described below.

A fragment of R2219_2AcDNA was amplified by RT-PCR method using poly(A) RNA of rice root as the template. The primers for the amplification of R2219_2A were R2219 2AU (SEQ ID NO:5 in the sequence list) as the sense primer and R2219 2AD (SEQ ID NO: 6 in the sequence list) as the antisense primer. The amplified region was found to contain the region corresponding to peptide No. 8.

For RT-PCR reaction, Takara RNA PCR kit was used. The PCR conditions were: 94° C. for 5 minutes, then 55° C. for 1 minute and 72° C. for one minute in one cycle; and then 94° C. for 1 minute, then 55° C. for 1 minute and 72° C. for one minute in 25 cycles.

Then, the Northern hybridization was carried out to elucidate whether soybean RNA had a sequence homologous to that of rice plant R2219_2A using above-described rice plant 2219 2Ac DNA.

The Northern blotting of the total RNA extracted from the respective organ of the soybeans was carried out by using R2219_2Ac DNA obtained as described above. The organ of the soybeans used were day three and day seven cotyledons after the germination, seven day shoots after the germination, immature cotyledons, pods and leaves.

After the hybridization at 55° C. or 60° C. followed by the stringent washing with 0.5×SSC, 0.1% SDS at a temperature equal to that of the hybridization, day seven shoots after the germination, produced a clear signal. The size thereof was calculated to be about 1.5 kbp.

From this result, it was concluded that the soybean shoots had mRNA having some homology to that of rice plant R2219_2A, and it was strongly expected to be GX mRNA. The above experiments indicated that GX cDNA would be most likely obtained by screening cDNA library prepared from mRNA of soybean shoots on the seventh day after the germination under the hybridization condition of 60° C. by using the rice plant R2219_2AcDNA as the probe.

<4> Screening for cDNA Library Derived from Germinated Soybean Shoots by Using Rice Plant EST as the Probe:

cDNA library 7.2×10$^4$ pfu prepared from polyA RNA of soybean seven day shoots after the germination was screened by an ordinary method under the above-described conditions to obtain seven hybridizing clones. The DNA sequence of each clone was determined to find a clone containing the full length GX DNA sequence of SEQ ID NO: 2, which encodes the polypeptide comprising amino acids of 487 residues of SEQ ID NO: 2 and which contains GX internal amino acd sequence of SEQ ID NO: 4.

It was considered that this DNA sequence was that of the intended GX cDNA because it encoded all of the 10 regions of GX internal amino acid sequences determined as stated above. Then, it was tried to produce GX protein by *E. coli* using this cDNA.

Example 2

Production of GX by *E coli*:

GX cDNA obtained in Example 1 was integrated into an expression vector which functions in *E. coli*, and transformants containing the expression plasmid were cultured. GX activity was detected in the cells. In addition to the sequence of the obtained GX cDNA, expression plasmids were also prepared for those in which the codons were changed in four residues ranging from Ala (the second residue from the N terminal) to Leu (the fifth residue), i.e. Ala, Ala, Lys and Leu, taking the codon usage for *E. coli* into consideration. The expression levels of them were compared with one another.

In this Example, the present invention will be illustrated on <1> the construction of expression plasmid, <2> the preparation of *E. coli* transformant using the expression plasmid and the culture thereof and <3> the determination of GX activity.

<1> Construction of Expression Plasmid:
(1) Construction of Expression Plasmid Having the Unmodifed Sequence of GX cDNA:

trp Promoter the transcription of which can be easily induced by the lacking of tryptophan in the medium was used as the promoter for transcribing GX genes. trp Promoter was used for plasmid pTTG-22 (JP-Kokai No.6-225775) which highly expressed Pagrus major transglutaminase (TG) genes. The sequence of the upstream of the Pagrus major TG gene was designed so that heterologous protein would be highly expressed in *E. coli*. Plasmid pUCTRPMTG(+)D2 (EP-A-0889133) which highly expressed transglutaminase (MTG) genes deiived from microorganisms had the upper stream sequence (SEQ ID NO: 3) containing trp promoter of the expression plasmid of Pagrus major TG. By the further integration into multi-copy plasmid pUC 19, MTG was highly expressed.

DNA fragment was linked to trp promoter to the upstream region of GX cDNA using PCR. At first, as shown in FIG. 1, the region (SEQ ID NO: 3) containing trp promoter of MTG expression plasmid pUCTRPMTG(+)D2 and the partial region of GX cDNA were amplified by PCR. The primers for amplifying trp promoter were TRP-N2 (SEQ ID NO. 7) and TRP-C2 (SEQ ID NO:8); the primers for amplifying GX were GX-N1 (SEQ ID NO:9) and GX-C (SEQ ID NO:10); TRP-N2 and GX-N1 were sense primers; and TRP-C2 and GX-C are antisense primers. GX-N1 was designed to add 11 bases DNA sequence which would be used for linking GX to the trp promoter containing fragment, immediately upstream the initiation codon of GX. This sequence is complementary to the sequence in TRP-C2.

PCR was conducted by using plasmid pUCTRPMTG(+) D2 and primers TRP-N2 and TRP-C2; and plasmid pR2219i containing the full length GX cDNA and primers GX-N1 and GX-C. The PCR reaction conditions were: 94° C. for 2 minutes in one cycle; and 94° C. for 30 seconds, then 50° C. for 5 seconds and 72° C. for 30 seconds in 25 cycles. The PCR products were treated with phenol/chloroform and then precipitated with ethanol. Each precipitant was dissolved in 100 µL of dH$_2$O.

Aliquot (1 µL) was taken from each of the PCR products and they were mixed. After the heat denaturation at 94° C. for 10 minutes, PCR was carried out by using primers TRP-N2 and GX-C for 25 cycles. The conditions in each cycle comprised 94° C. for 30 seconds, then 55° C. for 5 seconds and then 72° C. for 1 minute.

The second PCR product was extracted with phenol/chloroform. After the precipitation with ethanol, the product was digested with EcoRI and KpnI and then subcloned into pUC18 to obtain pUCTRPGXN1-8 (FIG. 1). The sequence was confirmed.

Figure 2:
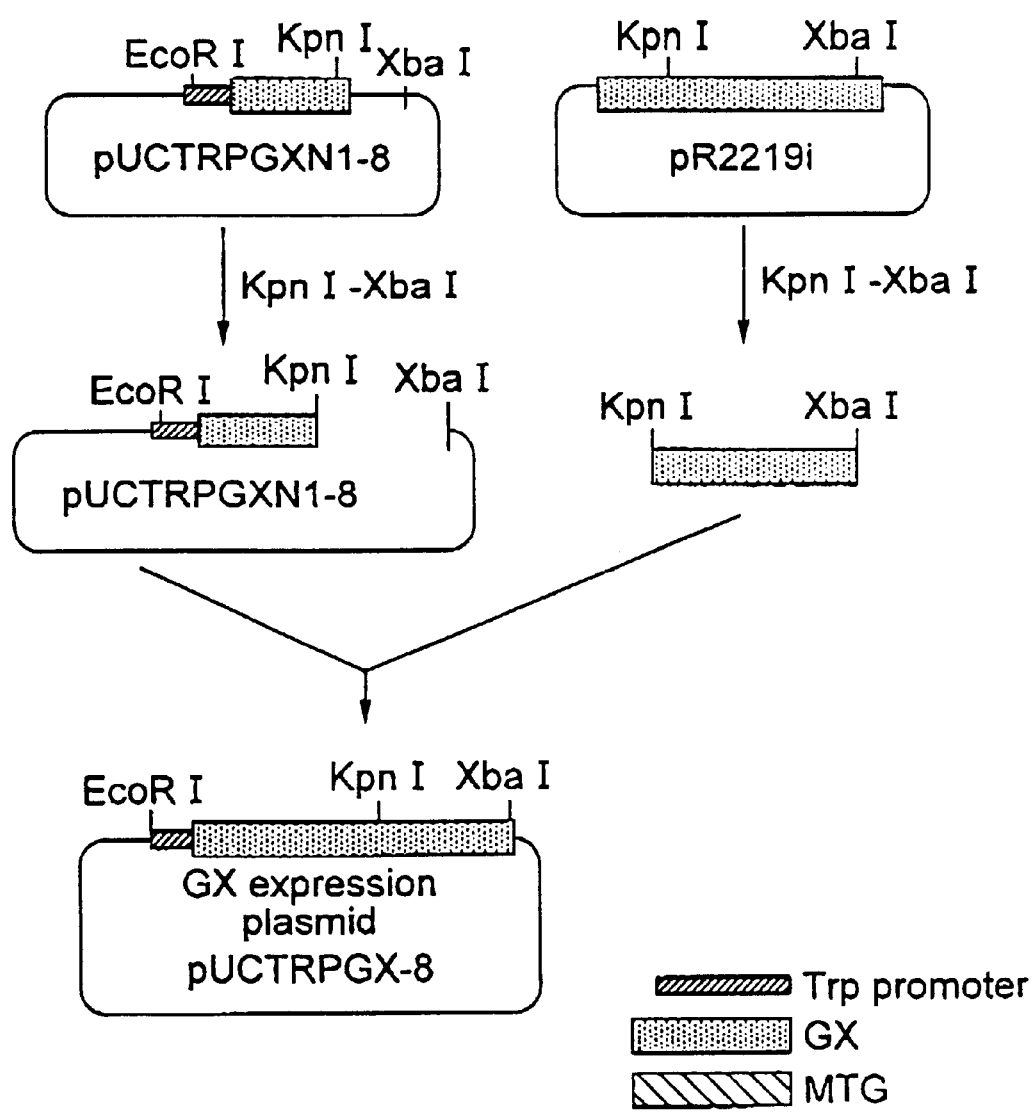
FIG. 2 shows the strategy for construction of GX expression plasmid pUCTRPGX1-8.

Then, C-terminal region of GX gene contained in pR2219i was excised using KpnI and XbaI and subcloned into the above-described pUCTRPGXN-1-8 to obtain GX expression plasmid pUCTRPGX1-8 driven by trp promoter (FIG. 2).

(2) Construction of GX Expression Plasmid with Modified Codons:

The plasmid was constructed in the same manner as that of above-described method (1) except that GX-N2 (SEQ ID NO:11) was used as the sense primer for the amplification of N-terminal segment of GX cDNA by PCR. In GX-N2, codons corresponding to the second to the fifth residues from the N-terminal, i. e. codons corresponding to Ala, Ala, Lys and Leu, were changed from GCG GCG AAG CTA (SEQ ID NO:12) to GCT GCT AAA CTG (SEQ ID NO:13).

PCR was conducted by using plasmid pUCTRPMTG(+) D2 and primers TRP-N2 and TRP-C2; or plasmid pR2219i and primers GX-N2 and GX-C. The PCR reaction conditions were: 94° C. for 2 minutes in one cycle; and 94° C. for 30 seconds, then 50° C. for 5 seconds and 72° C. for 30 seconds in 25 cycles. The PCR products were treated with phenol/chloroform and then precipitated with ethanol. Each product was dissolved in 100 μL of dH₂O.

Aliquot (1 μL) was taken from each of the PCR products and they were mixed. After heat denaturation at 94° C. for 10 minutes, PCR was carried out by using primers TRP-N2 and GX-C for 25 cycles. Conditions in each cycle comprised 94° C. for 30 seconds, then 55° C. for 5 seconds and then 72° C. for 1 minute.

Figure 3:
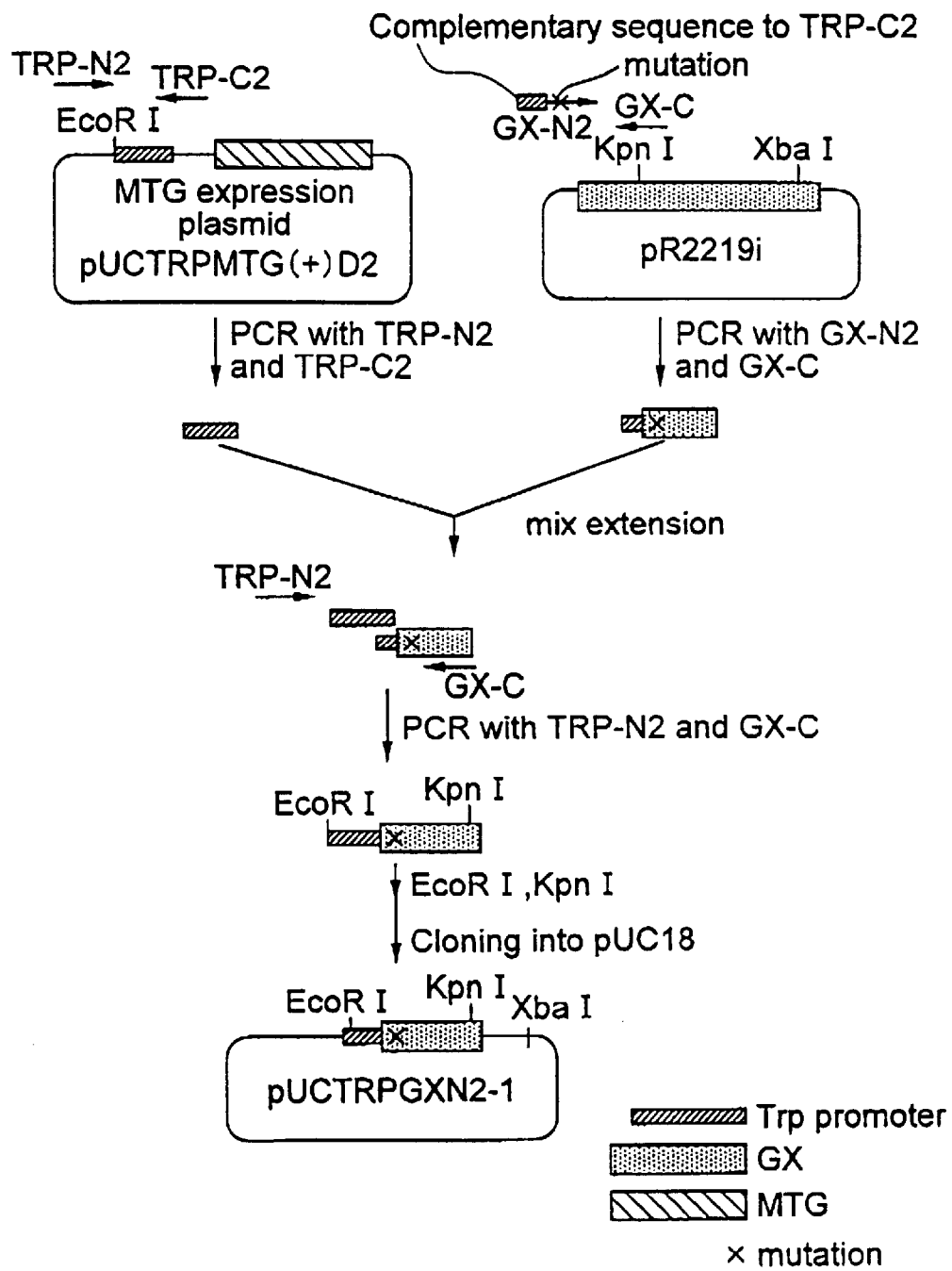
FIG. 3 shows the strategy for construction of plasmid pUCTRPGXN2-1.

The second PCR product was extracted with phenol/chloroform. After the precipitation wit ethanol, the product was digested with EcoRI and KpnI and then subcloned into pUC18 to obtain pUCTRPGXN2-1 (FIG. 3). The sequence was confirmed.

Figure 4:
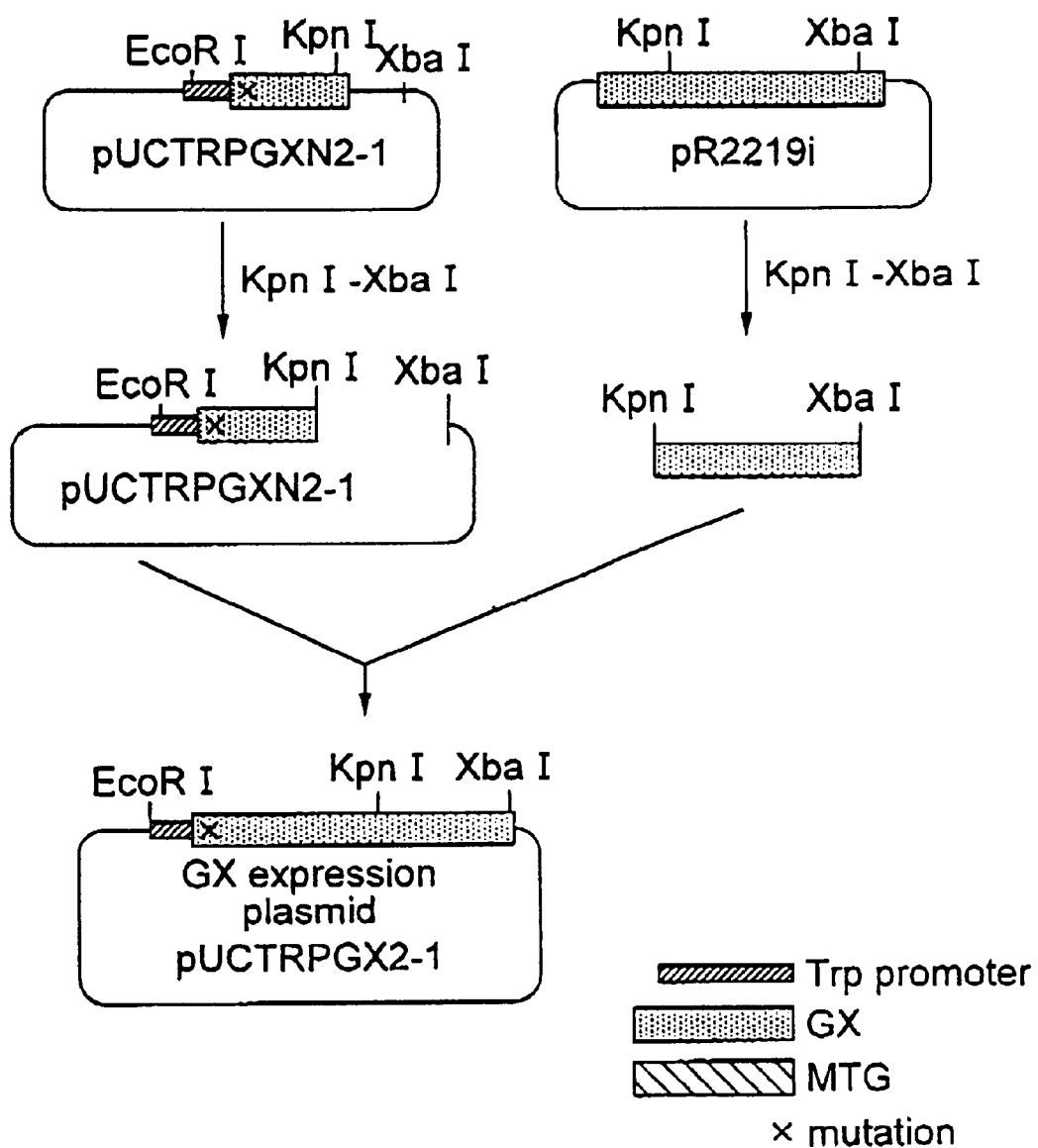
FIG. 4 shows the strategy for construction of GX expression plasmid pUCTRPGX2-1.

Then, C-terminal region of GX gene contained in pR2219i was excised by using KpnI and XbaI and subcloned into the above-described pUCTRPGXN2-1 to obtain GX expression plasmid pUCTRPGX2-1 driven by trp promoter (FIG. 4).

<2> Preparation and Culture of *E. coli* Transformant Using the Expression Plasmid pUCTRPGX2-1:

pUCTRPGX1-8, pUCTRPGX2-1 and pUC19 were introduced into *E. coli* JM109 by the competent cell method, and the transformant was selected in an agar medium containing 150 μg/mL of ampicillin. *E. coli* transformed with pUCTRPGX2-1 was named "AJ13564" and deposited in National Institute of Bioscience and Huma-Technology Agency of Industrial Science and Technology as FERM P-17131, which was relegated to international deposition in the same institute as FERM BP-7027 under the Budapest Treaty on Feb. 14, 2000. Each transformant was inoculated into 2×YT medium containing 150 μg/mL of ampicillin and cultured at 37° C. for 5 hours. 1 mL of the preculture liquid thus obtained was transferred into 50 mL of M9-Casamino acid medium containing 150 μg/mL of ampicillin to conduct the main culture. The main culture was conducted at 37° C. for 18 hours.

After the completion of the culture, the cells collected by the centrifugation were suspended in a cell-homogenizing buffer [50 mM Tris-HCl (pH 8.0), 5 mM EDTA] and the sonication was conducted with microchips of Branson MODEL-Sonifier 250 under conditions comprising output control 7, duty cycle 50% and about 10 minutes. The liquid thus obtained was centrifuged at 12,000 rpm for 10 minutes. The supernatant liquid was used as the soluble fraction in the cells, and the precipitates were used as the insoluble fraction. After the SDS-polyacrylamide gel electrophoresis, the expression of a protein having a molecular weight equal to that of GX was recognized in the pUCTRPGX1-8/JM109-soluble fraction, and in the pUCTRPGX2-1/JM109-soluble fraction and insoluble fraction. A particularly high expression was observed in the pUCTRPGX2-1/JM109-soluble fraction in which the codon had been modified. This fact clearly shows the effects obtained by changing the codon. A sufficiently high expression was obtained in the production medium even without the addition of 3-β-indoleacrylic acid.

<3> Determination of GX Activity:

The GX activity was determined on the basis of the increase in the amount of free glutamic acid due to the hydrolysis of dipeptide Glu-Glu. An enzyme solution was added to an activity determining solution containing 50 mM of HEPES (pH 8.0) and 5 mM of Glu-Glu. After carrying out the reaction at 37° C. for 5 to 10 minutes, acetic acid was added to the reaction mixture to the final concentration of 2% and thereby to terminate the reaction. The quantity of free glutamic acid was determined with a glutamic acid assay kit (a product of Seikagaku Kogyo). An activity for producing 1 μmol of glutamic acid in one minute was determined to be one unit.

GX activities of the soluble fractions of pUCTRPGX1-8/JM109, pUCTRPGX2-1/JM109 and pUC19/JM109, namely, the supernatant liquid containing the cell debris, were determined to calculate the specific activities. The specific activities obtained were 0.91 U/mg for pUCTRPGX1-8/JM109, 2.88 U/mg for pUCTRPGX2-1/JM109 and 0.04 U/mg for pUC19/JM109. It was thus confirmed that GX protein accumulated in the cells had the activity. It was also confirmed that by modifying the codon, about three times as much amount of GX protein was accumulated.

What is claimed is:

1. An isolated DNA molecule encoding an aminopeptidase derived from germinating soybean cotyledon and having an amino acid sequence of SEQ ID NO:2.

2. The DNA molecule of claim 1, which has the sequence of nucleotide No.22 to No.1482 of SEQ ID NO:1.

3. An isolated DNA molecule which can hybridize to the DNA molecule having the sequence of SEQ ID NO:1 in stringent conditions and encodes a protein having an aminopeptidase activity, wherein said stringent conditions comprise washing in 0.5×SSC at 55° C.

4. The DNA molecule of claim 1, wherein codon usage is optimized for *Escherichia coli*.

5. The DNA molecule of claim 4, wherein the codon for Ala$^2$-Ala$^3$-Lys$^4$-Leu$^5$ (amino acids 2 to 5 of SEQ ID NO:2) is GCTGCTAAACTG (SEQ ID NO:13).

6. A recombinant DNA molecule comprising the DNA molecule of claim 1.

7. A recombinant DNA molecule comprising the DNA molecule of claim 4.

8. The recombinant DNA molecule of claim 6, which is an expression vector.

9. The recombinant DNA molecule of claim 6, which is a high copy vector.

10. A host transformed with the DNA molecule of claim 1.

11. The transformed host of claim 10, which is a prokaryote.

12. The transformed host of claim 10, which is a eukaryote.

13. The transformed host of claim 11, which is *Escheiichia coli*.

14. An *Escherichia coli* cell transformed with the DNA molecule of claim 4.

15. The *Escherichia coli* cell of claim 14, deposited as FERM BP-7027.

16. A method of producing a protein having aminopeptidase activity, which comprises the steps of (i) culturing the transformed host of claim 13, (ii) expressing a protein having the aminopeptidase activity, and (iii) recovering the protein.

17. A recombinant DNA molecule comprising the DNA molecule of claim 1 functionally linked to a trp promoter.

* * * * *

SEQUENCE LISTING

```
<160> NUMBER OF SEQ ID NOS:  14

<210> SEQ ID NO 1
<211> LENGTH: 1657
<212> TYPE: DNA
<213> ORGANISM: Glycine max
<220> FEATURE:
<221> NAME/KEY: CDS
<222> LOCATION: (22)..(1482)

<400> SEQUENCE: 1
aaaattaaaa tctgaaaaac a atg gcg gcg aag cta gac acc cac gcc gtg         51
                        Met Ala Ala Lys Leu Asp Thr His Ala Val
                         1               5                  10 gct tcc gat ctg atc gac ttc ctc aac gct tct cca acg gct ttc cac         99
Ala Ser Asp Leu Ile Asp Phe Leu Asn Ala Ser Pro Thr Ala Phe His
                15                  20                  25 gcc gtc gac gag gca aag agg cgt ttg cgt agc gcg ggg tac cac caa        147
Ala Val Asp Glu Ala Lys Arg Arg Leu Arg Ser Ala Gly Tyr His Gln
             30                  35                  40 ctc tct gag gag agg gtg tgg gaa ctg caa ccg ggc aac aag tac ttc        195
```

```
                                          -continued

Leu Ser Glu Glu Arg Val Trp Glu Leu Gln Pro Gly Asn Lys Tyr Phe
            45                  50                  55 ttc acc aga aat cac tcc acc atc gtc gcc ttc gcc atc ggc aaa aag      243
Phe Thr Arg Asn His Ser Thr Ile Val Ala Phe Ala Ile Gly Lys Lys
        60                  65                  70 tac gtt gct gga aat gga ttc tac ata att ggg gct cac acg gat agt      291
Tyr Val Ala Gly Asn Gly Phe Tyr Ile Ile Gly Ala His Thr Asp Ser
75                  80                  85                  90 cct tgt ctc aaa ctc aag cct gtc acc aag gtt gtt aag gct ggg att      339
Pro Cys Leu Lys Leu Lys Pro Val Thr Lys Val Val Lys Ala Gly Ile
                95                  100                 105 ttg gag gtt ggt gtc caa acc tat gga ggt ggt ctg tgg cac aca tgg      387
Leu Glu Val Gly Val Gln Thr Tyr Gly Gly Gly Leu Trp His Thr Trp
            110                 115                 120 ttt gat cga gac ttg act gtg gcg ggg agg gtc atc gtg cgg gaa gag      435
Phe Asp Arg Asp Leu Thr Val Ala Gly Arg Val Ile Val Arg Glu Glu
        125                 130                 135 aat gct ggt tct gtt tcg tac tca cat cgc ctt gtt aga att gag gaa      483
Asn Ala Gly Ser Val Ser Tyr Ser His Arg Leu Val Arg Ile Glu Glu
140                 145                 150 cct ata atg cga ata ccg act ttg gca att cac ttg gac aag act gtt      531
Pro Ile Met Arg Ile Pro Thr Leu Ala Ile His Leu Asp Lys Thr Val
155                 160                 165                 170 aat gat gga ttc aaa ttt aac aac gag aat cac ctt att ccc atc ttg      579
Asn Asp Gly Phe Lys Phe Asn Asn Glu Asn His Leu Ile Pro Ile Leu
                175                 180                 185 gca aca tcg ctg aag ggt gag ctc aat aaa gtg tcc tct gaa aat ggt      627
Ala Thr Ser Leu Lys Gly Glu Leu Asn Lys Val Ser Ser Glu Asn Gly
            190                 195                 200 cct gtt gaa agt gga aat cag acc gat gga aag aaa gca aat gat aaa      675
Pro Val Glu Ser Gly Asn Gln Thr Asp Gly Lys Lys Ala Asn Asp Lys
        205                 210                 215 aca ggc acc agc aat acg aag cat cac ctt ctt ctt cta cag ttg ctt      723
Thr Gly Thr Ser Asn Thr Lys His His Leu Leu Leu Leu Gln Leu Leu
220                 225                 230 gca agc aag ctt ggg tgt gaa cca gat gac ata tgt gat ttt gaa ttg      771
Ala Ser Lys Leu Gly Cys Glu Pro Asp Asp Ile Cys Asp Phe Glu Leu
235                 240                 245                 250 caa gct tgc gat aca caa cca agt act att gct gga gct gca aag gaa      819
Gln Ala Cys Asp Thr Gln Pro Ser Thr Ile Ala Gly Ala Ala Lys Glu
                255                 260                 265 ttc att ttt tca gga cgg ctt gat aat ctc tgc atg tca ttt tgc tcg      867
Phe Ile Phe Ser Gly Arg Leu Asp Asn Leu Cys Met Ser Phe Cys Ser
            270                 275                 280 ctg aag gca tta ata gat gct aca tct tct gac agc agt ctt gag gaa      915
Leu Lys Ala Leu Ile Asp Ala Thr Ser Ser Asp Ser Ser Leu Glu Glu
        285                 290                 295 gag tca ggt gtt aga atg gtg gct tta ttt gac cat gag gaa gtt gga      963
Glu Ser Gly Val Arg Met Val Ala Leu Phe Asp His Glu Glu Val Gly
300                 305                 310 tct aac tct gcc caa gga gct ggc tct cct gtt atg cta aat act gtg     1011
Ser Asn Ser Ala Gln Gly Ala Gly Ser Pro Val Met Leu Asn Thr Val
315                 320                 325                 330 act agg gtt acc aat tcc ttc agc tcc aat ccc aac ctt ctg gag aaa     1059
Thr Arg Val Thr Asn Ser Phe Ser Ser Asn Pro Asn Leu Leu Glu Lys
                335                 340                 345 gca gca caa tta agc tac ctt gta tct gcc gac atg gca cat gca cta     1107
Ala Ala Gln Leu Ser Tyr Leu Val Ser Ala Asp Met Ala His Ala Leu
            350                 355                 360
```

```
cac cca aat tac atg gac aag cat gaa gca aac cat cag ccc aaa cta     1155
His Pro Asn Tyr Met Asp Lys His Glu Ala Asn His Gln Pro Lys Leu
        365                 370                 375 cat gga gga ctt gtc att aaa acc aat gca agc caa cgc tat gca acc     1203
His Gly Gly Leu Val Ile Lys Thr Asn Ala Ser Gln Arg Tyr Ala Thr
    380                 385                 390 aat gtt gtc aca tcc ttc ata ttc agg gag ata gca tca aaa cat aaa     1251
Asn Val Val Thr Ser Phe Ile Phe Arg Glu Ile Ala Ser Lys His Lys
395                 400                 405                 410 ctt ccc gtt cag gac ttt gtg gtg cgc aat gac atg tca tgt ggt tca     1299
Leu Pro Val Gln Asp Phe Val Val Arg Asn Asp Met Ser Cys Gly Ser
            415                 420                 425 acc att ggt cct att ctt gct agt ggc gta ggt att cgc act gtt gat     1347
Thr Ile Gly Pro Ile Leu Ala Ser Gly Val Gly Ile Arg Thr Val Asp
        430                 435                 440 gta ggt gca ccg cag ttg tca atg cat agc ata cga gaa att tgt gct     1395
Val Gly Ala Pro Gln Leu Ser Met His Ser Ile Arg Glu Ile Cys Ala
    445                 450                 455 gtt gat gat gtg aag tat tca tat gag cac ttc aaa gca ttt tac caa     1443
Val Asp Asp Val Lys Tyr Ser Tyr Glu His Phe Lys Ala Phe Tyr Gln
460                 465                 470 gaa ttc tct cat gtt gat ggt aag atg gtc gtg gat ata taggaatatc     1492
Glu Phe Ser His Val Asp Gly Lys Met Val Val Asp Ile
475                 480                 485 tctaatcacg aaatcctcat taatcctttg ctctagaagc tgttgctgaa atggtcgtgt   1552
ttcgtaattt agtaccatta taatgccgac gttattatga tgaattttc aataaaatta    1612 gactccctga atgaaatatt agcaactaaa aaaaaaaaaa aaaaa                   1657

<210> SEQ ID NO 2
<211> LENGTH: 487
<212> TYPE: PRT
<213> ORGANISM: Glycine max

<400> SEQUENCE: 2

Met Ala Ala Lys Leu Asp Thr His Ala Val Ala Ser Asp Leu Ile Asp
1               5                   10                  15

Phe Leu Asn Ala Ser Pro Thr Ala Phe His Ala Val Asp Glu Ala Lys
                20                  25                  30

Arg Arg Leu Arg Ser Ala Gly Tyr His Gln Leu Ser Glu Glu Arg Val
            35                  40                  45

Trp Glu Leu Gln Pro Gly Asn Lys Tyr Phe Phe Thr Arg Asn His Ser
        50                  55                  60

Thr Ile Val Ala Phe Ala Ile Gly Lys Lys Tyr Val Ala Gly Asn Gly
65                  70                  75                  80

Phe Tyr Ile Ile Gly Ala His Thr Asp Ser Pro Cys Leu Lys Leu Lys
                85                  90                  95

Pro Val Thr Lys Val Val Lys Ala Gly Ile Leu Glu Val Gly Val Gln
            100                 105                 110

Thr Tyr Gly Gly Gly Leu Trp His Thr Trp Phe Asp Arg Asp Leu Thr
        115                 120                 125

Val Ala Gly Arg Val Ile Val Arg Glu Glu Asn Ala Gly Ser Val Ser
    130                 135                 140

Tyr Ser His Arg Leu Val Arg Ile Glu Glu Pro Ile Met Arg Ile Pro
145                 150                 155                 160

Thr Leu Ala Ile His Leu Asp Lys Thr Val Asn Asp Gly Phe Lys Phe
                165                 170                 175
```

```
Asn Asn Glu Asn His Leu Ile Pro Ile Leu Ala Thr Ser Leu Lys Gly
            180                 185                 190
Glu Leu Asn Lys Val Ser Ser Glu Asn Gly Pro Val Glu Ser Gly Asn
            195                 200                 205
Gln Thr Asp Gly Lys Lys Ala Asn Asp Lys Thr Gly Thr Ser Asn Thr
            210                 215                 220
Lys His His Leu Leu Leu Gln Leu Leu Ala Ser Lys Leu Gly Cys
225                 230                 235                 240
Glu Pro Asp Asp Ile Cys Asp Phe Glu Leu Gln Ala Cys Asp Thr Gln
                    245                 250                 255
Pro Ser Thr Ile Ala Gly Ala Lys Glu Phe Ile Phe Ser Gly Arg
            260                 265                 270
Leu Asp Asn Leu Cys Met Ser Phe Cys Ser Leu Lys Ala Leu Ile Asp
            275                 280                 285
Ala Thr Ser Ser Asp Ser Ser Leu Glu Glu Ser Gly Val Arg Met
            290                 295                 300
Val Ala Leu Phe Asp His Glu Glu Val Gly Ser Asn Ser Ala Gln Gly
305                 310                 315                 320
Ala Gly Ser Pro Val Met Leu Asn Thr Val Thr Arg Val Thr Asn Ser
                    325                 330                 335
Phe Ser Ser Asn Pro Asn Leu Leu Glu Lys Ala Ala Gln Leu Ser Tyr
            340                 345                 350
Leu Val Ser Ala Asp Met Ala His Ala Leu His Pro Asn Tyr Met Asp
            355                 360                 365
Lys His Glu Ala Asn His Gln Pro Lys Leu His Gly Gly Leu Val Ile
            370                 375                 380
Lys Thr Asn Ala Ser Gln Arg Tyr Ala Thr Asn Val Val Thr Ser Phe
385                 390                 395                 400
Ile Phe Arg Glu Ile Ala Ser Lys His Lys Leu Pro Val Gln Asp Phe
                    405                 410                 415
Val Val Arg Asn Asp Met Ser Cys Gly Ser Thr Ile Gly Pro Ile Leu
            420                 425                 430
Ala Ser Gly Val Gly Ile Arg Thr Val Asp Val Gly Ala Pro Gln Leu
            435                 440                 445
Ser Met His Ser Ile Arg Glu Ile Cys Ala Val Asp Asp Val Lys Tyr
            450                 455                 460
Ser Tyr Glu His Phe Lys Ala Phe Tyr Gln Glu Phe Ser His Val Asp
465                 470                 475                 480
Gly Lys Met Val Val Asp Ile
                485

<210> SEQ ID NO 3
<211> LENGTH: 357
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
cgcccaatac gcaaaccgcc tctccccgcg cgttggccgc ttcattaatg cagctggcac      60
gacaggtttc ccgactggaa agcgggcagt gagcgcaacg caattaatgt gagttagctc     120
actcattagg caccccaggc tttacacttt atgcttccgg atcgtatgtt gtgtggaatt     180
gtgagcggat aacaatttca cacaggaaac agctatgacc atgattacgc caagcttgca     240
```

```
tgcctgcagg tcgcccttc gtcttcaaga attcccctgt tgacaattaa tcatcgaact      300
agttaactag tacgcaagtt cacgtaaaaa gggtatcgat tagtaaggag gtttaaa         357
```

<210> SEQ ID NO 4
<211> LENGTH: 20
<212> TYPE: PRT
<213> ORGANISM: Glycine max

<400> SEQUENCE: 4

```
Ser Ala Gly Tyr His Gln Leu Ser Glu Arg Glu Val Trp Glu Leu Gln
 1               5                  10                  15

Pro Gly Asn Lys
            20
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5

```
ctacacctga ctcatcgatc cacta                                             25
```

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6

```
caggcttgag cttcagggat ggact                                             25
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7

```
cgcccaatac gcaaaccgcc                                                   20
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 8

```
tttaaacctc cttactaatc gataccc                                           27
```

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:synthetic
      DNA

```
<400> SEQUENCE: 9
ggaggtttaa aatggcggcg aagctagaca cc                              32

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 10
gttgcagttc ccacaattcc c                                          21

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 11
ggaggtttaa aatggctgct aaactggaca cc                              32

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 12
gcggcgaagc ta                                                    12

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 13
gctgctaaac tg                                                    12

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 14

Ala Ala Lys Leu
```